(12) United States Patent
Sharp et al.

(10) Patent No.: US 11,707,453 B2
(45) Date of Patent: Jul. 25, 2023

(54) TREATMENT OF UNIPOLAR DEPRESSIVE DISORDER

(71) Applicant: OXFORD UNIVERSITY INNOVATION LIMITED, Oxford (GB)

(72) Inventors: Trevor Sharp, Oxford (GB); Philip Cowen, Oxford (GB); Grant Churchill, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 127 days.

(21) Appl. No.: 16/758,642

(22) PCT Filed: Oct. 26, 2018

(86) PCT No.: PCT/GB2018/053101
§ 371 (c)(1),
(2) Date: Apr. 23, 2020

(87) PCT Pub. No.: WO2019/081942
PCT Pub. Date: May 2, 2019

(65) Prior Publication Data
US 2021/0000803 A1 Jan. 7, 2021

(30) Foreign Application Priority Data
Oct. 26, 2017 (GB) ...................... 1717629

(51) Int. Cl.
*A61K 31/428* (2006.01)
*A61P 25/24* (2006.01)
*A61K 9/00* (2006.01)

(52) U.S. Cl.
CPC .......... *A61K 31/428* (2013.01); *A61K 9/0053* (2013.01); *A61P 25/24* (2018.01)

(58) Field of Classification Search
CPC ...... A61K 31/428; A61K 9/0053; A61P 25/24
See application file for complete search history.

(56) References Cited

U.S. PATENT DOCUMENTS

| 4,935,429 A | 6/1990 | Dackis et al. |
| 4,981,980 A | 1/1991 | Giocobbe et al. |

(Continued)

FOREIGN PATENT DOCUMENTS

| EP | 1884234 A1 | 2/2008 |
| JP | 2008007446 A | 1/2008 |

(Continued)

OTHER PUBLICATIONS

Souery et al., J clin Psychiatry, 2006;67 (suppl 6):16-22 (Year: 2006).*

(Continued)

*Primary Examiner* — San Ming R Hui
(74) *Attorney, Agent, or Firm* — Liang & Hennessey LLP; Stanley D. Liang

(57) ABSTRACT

The invention relates to the treatment or control of unipolar depressive disorder by administering a compound of Formula I or a salt thereof to a subject;

Formula I

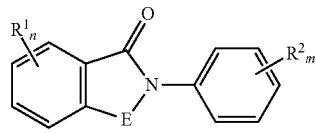

wherein:
E is S or Se;
$R^1$ and $R^2$ are optional substituents, and are at each occurrence independently selected from:

(Continued)

(1) a halogen, which is preferably selected from F, Cl and Br;
(2) $C_1$-$C_4$ alkyl, such as $C_1$-$C_2$ alkyl or $C_1$ alkyl, optionally substituted with one or more halogen atoms, each of which is preferably selected from F, Cl and Br; and
(3) $C_1$-$C_4$ alkoxy, such as $C_1$-$C_2$ alkoxy or $C_1$ alkoxy; optionally substituted with one or more halogen atoms, each of which is preferably selected from F, Cl and Br;
m is an integer in the range of from 0 to 5; and
n is an integer in the range of from 0 to 4.

9 Claims, 15 Drawing Sheets

(56) References Cited

U.S. PATENT DOCUMENTS

| | | |
|---|---|---|
| 6,001,848 A | 12/1999 | Noble |
| 10,653,680 B2 | 5/2020 | Rogers et al. |
| 2014/0094449 A1 | 4/2014 | Churchill et al. |
| 2017/0246148 A1 | 8/2017 | Kil |

FOREIGN PATENT DOCUMENTS

| | | | |
|---|---|---|---|
| WO | 9949860 A1 | 10/1999 | |
| WO | WO-9949860 A1 * | 10/1999 | ............. A61K 31/00 |
| WO | 2006096759 A2 | 9/2006 | |
| WO | 2006123676 A1 | 11/2006 | |
| WO | 2012107735 A2 | 8/2012 | |
| WO | 2015200358 A1 | 12/2015 | |

OTHER PUBLICATIONS

International Search Report and Written Opinion in International Application No. PCT/GB2018/053101, dated Feb. 27, 2019, 15 pages.
Antoniadou et al., "Effect of Ebselen, A Putative Lithium-mimetic on Central 5HT2A Receptor Function in the Mouse", Internet Citation, Dec. 13, 2011, pp. 1.
Dominique Januel et al., "Interaction of Lithium with 5-HT1B Receptors in Depressed Unipolar Patients Treated with Clomipramine and Lithium Versus Clomipramine and Placebo: Preliminary Results", Psychiatry Research, Aug. 1, 2002, vol. 111, No. 2-3, pp. 117-124.
UKIPO Search Report in GB Application No. GB1717629.8, dated Aug. 15, 2018, 5 pages.
T Posser et al., "Antidepressant-like Effect of the Organoselenium Compound Ebselen in Mice: Evidence for the Involvement of the Monoaminergic System", Eur. J. Pharmacology, Nov. 9, 2008, vol. 62, No. 09, pp. 85-91.
Antoniadou et al., "Effect of Lithium and Ebselen, A Noveel Inhibitor of Inositol Monophosphatase, on Molecule Markers of Neuronal Plasticity in the Mouse", Proceedings of the British Pharmacological Society, Dec. 2013, pp. 1-3.
Atack, et al., "Inositol Monophosphatase—a Putative Target for Li+ in the Treatment of Bipolar Disorder", Trends N Neurosciences, 18(8), 1995, 343-349.
GB Search Report received in GB1607388.4 dated Feb. 15, 2018 (3 pages).
Hollander, et al., "Does Sustained-Release Lithium Reduce Impulsive Gambling and Affective Instability Versus Placebo in Pathological Gamblers With Bipolar Spectrum Disorders", American Journal of Psychiatry., 162 (1), Jan. 1, 2005, 137-145, pp. 9.
International Search Report & Written Opinion received in PCT/GB2017/051174 dated Jun. 22, 2017 (13 pages).
Ledesma, et al., "Reduction in Central $H_2O_2$ Levels Prevents Voluntary Ethanol Intake in Mice: A Role for the Brain Catalase—$H_2O_2$ System in Alcohol Binge Drinking", Alcoholism: Clinical and Experimental Research, 38(1), Jan. 1, 2014, 60-67, pp. 2.
Masaki, et al., "Effects of the Potential Lithium-mimetic, Ebselen, on Impulsivity and Emotional Processing", Psychopharmacology, Springer Verlag, Berlin, De, 233(14), Jun. 2, 2016, 2655-2661, pp. 12.
Singh, et al., "A Safe Lithium Mimetic for Bipolar Disorder", Nature Communications, 4, Jan. 8, 2013, 1332., pp. 7.
Singh, et al., "Effect of the Putative Lithium Mimetic Ebselen on Brain Myo-Inositol, Sleep, and Emotional Processing in Humans", Neuropsychopharmacology, 41(7), Nov. 23, 2015, 1768-1778, pp. 11.
Office Action received in U.S. Appl. No. 16/097,239 dated Jun. 14, 2019.

* cited by examiner

TREATMENT OF UNIPOLAR DEPRESSIVE DISORDER

TECHNICAL FIELD

The present invention relates to the treatment of unipolar depressive disorder, in particular to the treatment or control of treatment-resistant unipolar depressive disorder, and to compounds that can be used to treat or control such disorders.

BACKGROUND

NICE (www.nice.org.uk) defines treatment-resistant depressive disorder as that which fails to respond to two or more antidepressants given sequentially at an adequate does for an adequate time. Gaynes et al state that 'having two adequately dosed but unsuccessful treatment trials in the same episode predicts a lower likelihood to remission with the next treatment (https://www.guideline.gov/expert/expert-commentary/36835/primary-care-depressive disorder-guidelines-and-treatment-resistant-depressive disorder-variations-on-an-important-but-understudied-theme) and that the likelihood of recovery with a subsequent treatment decreases to approximately 15%.

Lithium is valuable as an augmentation agent in treatment-resistant unipolar depressive disorder (Cipriani et al., 2005, The American journal of psychiatry 162: 1805-1819; Fountoulakis et al., 2012, Eur. Arch. Psych. Clin. Neurosci. 262 Suppl 1: 1-48; Geddes & Miklowitz, 2013, Lancet 381: 1672-1682). However, the full therapeutic potential of lithium is limited by poor tolerance and low treatment compliance due to poor tolerability, a narrow therapeutic window, longer-term toxicity, particularly for the kidneys, and the risk of teratogenicity. Furthermore, studies report a response rate of about 50% over four weeks of combined lithium-tricyclic antidepressant treatment (Price et al, 1986, American Journal of Psychiatry, 143, 1387-1392).

Development of improved treatments has been hindered by a lack of understanding of the mechanism of action of lithium, which interacts non-selectively with a number of neurotransmitters and receptors. There are a number of competing hypotheses for the mechanism of action of lithium, including; facilitation of serotonin function (Cowen et al, 1991. Lithium in tricyclic-resistant depressive disorder. Correlation of increased brain 5-HT function with clinical outcome. *The British Journal of Psychiatry*, 159(3), pp. 341-346.); inhibition of glycogen synthase kinase (GSK-3) (Gould & Manji, 2005, Neuropsychopharmacology 30: 1223-1237); and the 'inositol depletion' hypothesis (Berridge et al., 1989, Cell 59: 411-419; Mahli et al., 2013, CNS Drugs 27(2):135-53). Six decades after the introduction of lithium, and over thirty years since the first reported use of Lithium as an augmentation agent in treatment-resistant depressive disorder, there remains no approved alternative to this poorly tolerated molecule.

WO2012/1207735 A discusses the use of the compound ebselen in the treatment of bipolar disorder, a disorder which is characterised by recurrent episodes of mania or elevated mood, and irritable or depressive moods. Bipolar disorder is distinct from other mood disorders, such as unipolar depressive disorder and recurrent unipolar depressive disorder and is separately classified in the World Health Organisation's International Statistical Classification of Diseases and Related Health Problems.

Therefore, there is a clear need for alternative treatments for chronic or treatment resistant unipolar depressive disorder with improved tolerability, which can be used in a wider clinical population, and which have better compatibility with other commonly used drugs.

SUMMARY OF INVENTION

According to the present invention, there is provided a compound of Formula I, or a pharmaceutically acceptable salt thereof, for use in the treatment or control of treatment-resistant unipolar depressive disorder

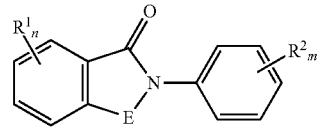

Formula I wherein:
E is S or Se;
$R^1$ and $R^2$ are optional substituents, and are at each occurrence independently selected from:
(1) a halogen, which is preferably selected from F, Cl and Br;
(2) $C_1$-$C_4$ alkyl, such as $C_1$-$C_2$ alkyl or $C_1$ alkyl, optionally substituted with one or more halogen atoms, each of which is preferably selected from F, Cl and Br; and
(3) $C_1$-$C_4$ alkoxy, such as $C_1$-$C_2$ alkoxy or $C_1$ alkoxy; optionally substituted with one or more halogen atoms, each of which is preferably selected from F, Cl and Br;
m is an integer in the range of from 0 to 5; and
n is an integer in the range of from 0 to 4.

In another embodiment, the invention provides the compound 2-phenyl-1,2-benzisoselenazol-3(2H)-one (ebselen), or a pharmaceutically acceptable salt thereof, for use in the treatment or control of treatment-resistant unipolar depressive disorder.

The invention further relates to a pharmaceutical composition comprising a) a compound of Formula I, or a pharmaceutically acceptable salt thereof; b) one or more additional antidepressants or a pharmaceutically acceptable salt thereof; and c) one or more pharmaceutically acceptable excipients.

The invention further relates to methods of treating or controlling treatment-resistant unipolar depressive disorder, by administering to a subject a therapeutically effective amount of a compound of Formula I or a pharmaceutically acceptable salt thereof, or a pharmaceutical composition comprising a compound of Formula I or a pharmaceutically acceptable salt thereof.

The invention further relates to the use of a compound of Formula I, or a pharmaceutically acceptable salt thereof, in the manufacture of a medicament for the treatment or control of treatment-resistant unipolar depressive disorder.

The invention further provides a combination of: a) a compound of Formula I, or a pharmaceutically acceptable salt thereof; b) one or more additional antidepressants or a pharmaceutically acceptable salt thereof.

The invention further provides a kit comprising a) a compound of Formula I, or a pharmaceutically acceptable salt thereof, and b) one or more additional antidepressants or a pharmaceutically acceptable salt thereof.

BRIEF DESCRIPTION OF THE DRAWINGS

The present invention will now be described with reference to the accompanying drawings.

DETAILED DESCRIPTION

Figure 1A:
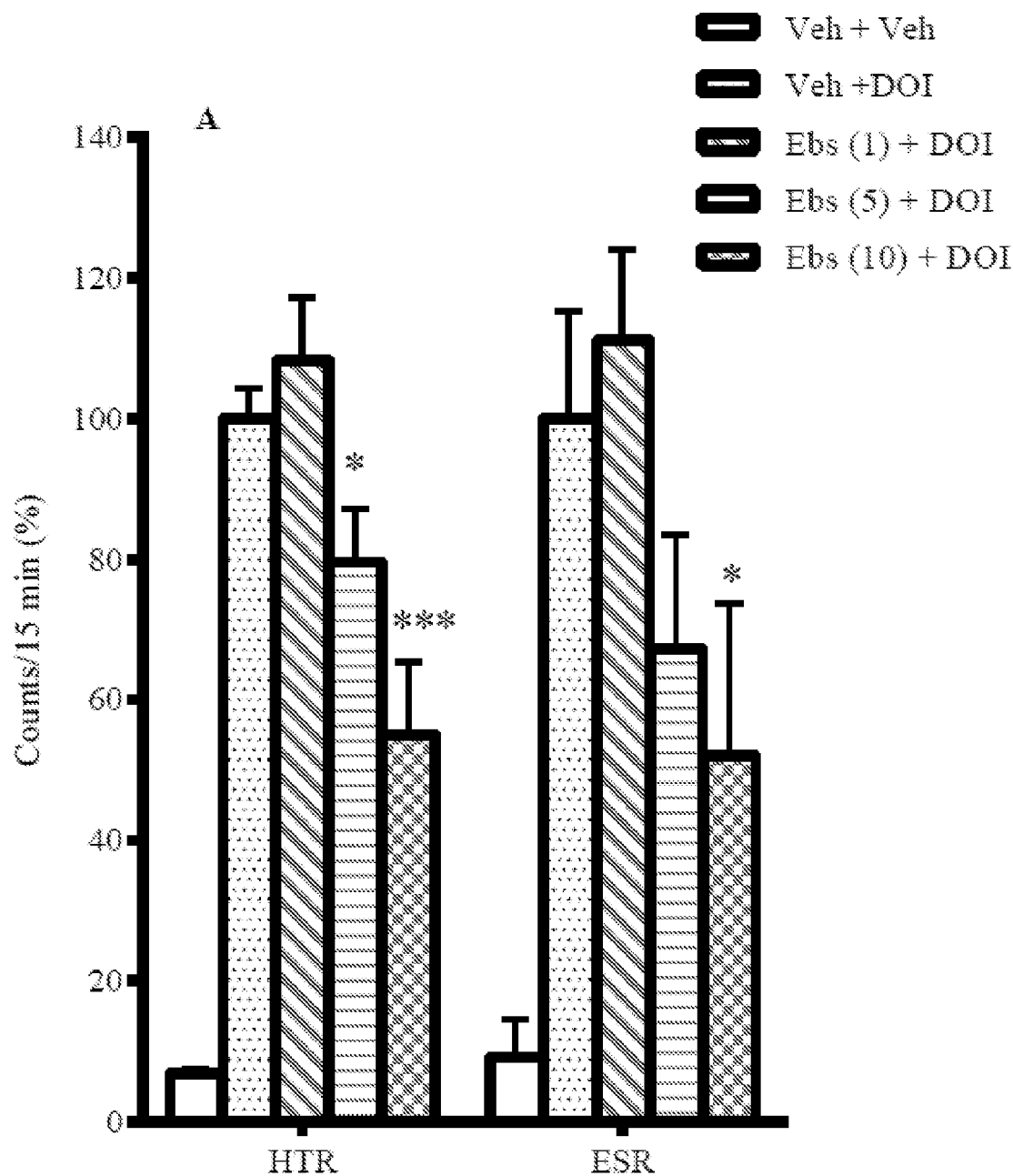
FIG. 1 shows the effect of ebselen on DOI-evoked behavioural responses.

It has now been found that the compounds of Formula I inhibit behavioural and IEG responses to the 5-$HT_{2A}$ receptor agonist DOI in an animal model, and hence are useful in the treatment or control of unipolar depressive disorder, particularly treatment-resistant unipolar depressive disorder.

In a first embodiment, the invention provides a compound of Formula I, or a pharmaceutically acceptable salt thereof, for use in the treatment or control of treatment-resistant unipolar depressive disorder

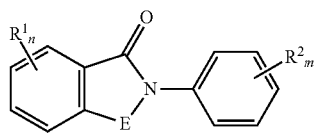

Formula I wherein, E is S or Se:

$R^1$ and $R^2$ are at each occurrence independently selected from:

(1) a halogen, which is preferably selected from F, Cl and Br;

(2) $C_1$-$C_4$ alkyl, such as $C_1$-$C_2$ alkyl or $C_1$ alkyl, optionally substituted with one or more halogen atoms, each of which is preferably selected from F, Cl and Br; and (3) $C_1$-$C_4$ alkoxy, such as $C_1$-$C_2$ alkoxy or $C_1$ alkoxy; optionally substituted with one or more halogen atoms, each of which is preferably selected from F, Cl and Br.

m is an integer in the range of from 0 to 5.

n is an integer in the range of from 0 to 4.

In a second embodiment, the invention provides a compound for use according to the first embodiment, wherein n and m are each independently 0, 1 or 2; preferably n and m are each independently 0 or 1; more preferably, only one of n and m is greater than zero, and more preferably the non-zero value is 1; most preferably, both n and m are zero.

In a third embodiment, the invention provides a compound for use according to any previous embodiment, wherein E is Se.

In a fourth embodiment, the invention provides a compound for use according to any preceding embodiment, wherein the compound of Formula I is 2-phenyl-1,2-benzisoselenazol-3(2H)-one (otherwise known as ebselen) or a pharmaceutically acceptable salt thereof. The structure of 2-phenyl-1,2-benzisoselenazol-3(2H)-one (ebselen) is shown in Formula II.

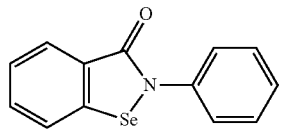

Formula II

In a fifth embodiment, the invention provides a compound for use according to the first or second embodiment wherein E is S.

In a sixth embodiment, the invention provides a compound for use according to the fifth embodiment, wherein the compound of Formula I is 2-phenyl-1,2-benzisothiazol-3(2H)-one, or a pharmaceutically acceptable salt thereof. The structure of 2-phenyl-1,2-benzisothiazol-3 (2H)-one is shown in Formula III below:

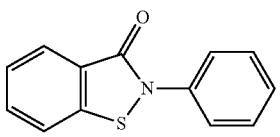

Formula III

In a seventh embodiment, the invention provides a compound for use according to any preceding embodiment, wherein the compound has the structure of Formula I, more preferably the compound has the structure of Formula II or Formula III.

In a further embodiment, the invention provides methods of treating or controlling treatment-resistant unipolar depressive disorder, comprising administering to a subject a therapeutically effective amount of a compound of Formula I or a pharmaceutically acceptable salt thereof, wherein the compound of Formula I is as defined in any one of the first to seventh embodiments.

In a further embodiment, the invention provides the use of a compound of Formula I, or a pharmaceutically acceptable salt thereof, in the manufacture of a medicament for the treatment or control of treatment-resistant unipolar depressive disorder, wherein the compound of Formula I is as defined in any one of the first to seventh embodiments.

It has been reported that Ebselen is capable of transferring across the blood/brain barrier (WO 2012/107735). Ebselen is also known to be sufficiently non-toxic in humans at pharmaceutically effective dosages, having already been through clinical trials for treating ischemic stroke (Yamaguchi et al; Stroke, 1998, 29, 12-17) and hence is a strong candidate for future clinical trials. The LD50 concentration of ebselen is greater than 1000 mg/kg in rats.

The compound of Formula I, preferably Ebselen or 2-phenyl-1,2-benzisothiazol-3(2H)-one, can be provided in the form of a pharmaceutically acceptable salt. Suitable pharmaceutically acceptable salts include this listed in by P. H. Stahl and C. G. Wermuth, editors, in *Handbook of Pharmaceutical Salts: Properties, Selection and Use*, 2002. Examples of suitable salts include salts formed with an inorganic acid such as hydrochloric acid, nitric acid or sulfuric acid; and salts formed with an organic acid such as acetic acid, fumaric acid, maleic acid, succinic acid or tartaric acid.

The compounds of Formula I can be formulated as outlined below, and in the dosages as described below.

Formulations

The compounds of Formula I described herein, or pharmaceutically acceptable salts thereof, can be delivered to a patient by intradermal, intramuscular, intraperitoneal, intravenous, subcutaneous, intranasal, or oral routes, for example. They can be administered by any convenient means, for example by infusion or bolus injection, by absorption through epithelial or mucotaneous linings (e.g. oral mucosa, rectal and intestinal mucosa). Administration can be systemic or local.

The compounds of Formula I described herein, or pharmaceutically acceptable salts, thereof, can be formulated as a medicament, which preferably takes the form of therapeutically effective individual doses of the compound of Formula I or salt thereof, adjusted to the form of administration.

For oral administration, the medicament can be formulated into solid or liquid preparations, such as pills, tablets, troches, capsules, powder, granules, syrups, solutions, suspensions or emulsions.

Solid medicaments can comprise one or more of the following in addition to the desired quantity of the compound of Formula I or salt thereof: a pharmaceutically active carrier, including conventional ingredients such as lactose, sucrose and cornstarch; binders such as acacia, cornstarch or gelatine; disintegrating agents, such as potato starch or alginic acid; and lubricants such as stearic acid or magnesium stearate. Optionally, the medicament can be a sustained release formulation, in which the ebselen is incorporated in a matrix of an acrylic polymer or chitin, for example.

Examples of liquid medicaments for oral administration include aqueous solutions such as syrups, flavoured syrups, aqueous or oil suspensions, optionally flavoured emulsions with edible oils, and elixirs. Suspensions can include dispersing or suspending agents such as synthetic and natural gums, for example tragacanth, acacia, alginate, dextran, sodium carboxymethylcellulose, methylcellulose, polyvinylpyrrolidone and gelatin.

For parenterally-administered medicaments, the compound of Formula I or salt thereof is typically formulated with a suitable liquid injection vehicle, which include for example water, saline, dextrose, water-miscible solvents such as ethanol, polyethylene glycol and propylene glycol, and non-aqueous vehicles such as plant or animal oils. Optionally, the medicament can be an emulsion. Optionally, the pH is typically in the range of from 6 to 8, preferably 6.5 to 7.5. Optionally, buffers such as citrates, acetates or phosphates, can be present. Optionally, antioxidants such as ascorbic acid or sodium bisulphite can be present. Optionally, solubilising agents and stabilisers such as cyclodextrin, lysolecithin, oleic acid, stearic acid, and dextrin can be present. Optionally, local anaesthetics such as lignocaine and procaine hydrochloridecan can be present. Formulations such as those described in US 2004/0029934, comprising phosphatidylcholine and phosphatidylethanolamine, and those described in US 2004/0053888 comprising cyclodextrin, can be used.

Doses

The compounds of Formula I, or salt thereof, are suitable for treating a mammalian subject, for example a human.

Suitable doses of the compound of Formula I or salt thereof are in the range of from 5 to 5000 mg for a human patient per day, for example from 50 to 2000 mg per day, from 200 to 1000 mg per day, or from 200 to 600 mg per day.

The compound of Formula I or salt thereof can be provided in one dose, or more than one dose, typically in the range of from two to eight doses per day, for example from two to four or from two to three doses per day. In one embodiment, the compound of Formula I or salt thereof can be administered in the form of an orally administered solution or suspension in water. An example of a dosage regime would be the administration of a solution or suspension comprising 100 mg of the compound of Formula I or salt thereof in water 3 times per day, or 150 mg in water twice daily. In another embodiment, capsules, pills or tablets comprising the compound of Formula I or salt thereof for oral administration can be provided, for example the administration of 1, 2, 3, 4 or 8 capsules, pills or tablets each comprising 200 mg of the compound of Formula I or salt thereof per day.

Typically, for human administration, each individual dose comprises in the range of from 5 to 500 mg of the compound of Formula I, or salt thereof, for example from 50 to 400 mg, or from 100 to 300 mg, such as 200 mg.

Combinations

The compounds or salts described herein can be administered in combination with one or more further compounds.

For example, a compound of Formula I, or pharmaceutically acceptable salt thereof, may be used in combination with another compound of Formula I, or a pharmaceutically acceptable salt thereof.

Alternatively, or additionally, one or more compounds of Formula I (or pharmaceutically acceptable salt thereof) can be used in combination with one or more additional antidepressants.

In a further embodiment, the invention provides a combination of a) a compound of Formula I or a pharmaceutically acceptable salt thereof, as defined in any one of the first to seventh embodiments; and b) one or more additional antidepressants or a pharmaceutically acceptable salt thereof.

In a further embodiment, the invention provides a combination of a) a compound of Formula I or a pharmaceutically acceptable salt thereof, as defined in any one of the first to seventh embodiments; and b) one or more additional antidepressants or a pharmaceutically acceptable salt thereof; for use in the treatment of treatment-resistant unipolar depressive disorder, wherein the combination is for separate or simultaneous administration Preferably the compound of Formula I is the compound of Formula II or the compound of Formula III. Preferably the additional antidepressant is selected from those listed hereinbelow.

In a further embodiment, the invention provides the combination of a) a compound of Formula I or a pharmaceutically acceptable salt thereof as defined in any one of the first to seventh embodiments, and b) one or more additional antidepressants selected from:

i. Selective Serotonin Reuptake Inhibitors (SSRIs), including citalopram, dapoxetine, escitalopram, fluoxetine, fluvoxamine, paroxetine and sertraline; and the related compound, vortioxetine;
ii. Tricyclic antidepressants (TCAs), including amitriptyline, clomipramine, dosulepin, doxepin, imipramine, lofepramine, and nortriptyline; and the related compound trazodone;
iii. Serotonin and Noradrenaline Reuptake inhibitors (SNRIs), including duloxetine, and venlafaxine;
iv. Noradrenergic and Specific Serotonergic Antidepressants, including mirtazapine;
v. Monoamine oxidase inhibitors (MAOIs), including moclobemide, phenelzine, tranylcypromine, isocarboxazid;
vi. Selective Noradrenaline Reuptake Inhibitors (NARI), including reboxetine;

vii. Noradrenaline and Dopamine Reuptake Inhibitors (NDRI), including bupropion;
viii. Melatonin agonists and 5-HT2C receptor antagonists, including agomelatine; and
ix. Lithium;
or a pharmaceutically acceptable salt thereof.

In a further embodiment, the invention provides the combination of a) a compound of Formula I or a pharmaceutically acceptable salt thereof as defined in any one of the first to seventh embodiments, and b) a Selective Serotonin Reuptake Inhibitor (SSRI) or a pharmaceutically acceptable salt thereof. Preferably the SSRI is selected from citalopram, dapoxetine, escitalopram, fluoxetine, fluvoxamine, paroxetine and sertraline, or a pharmaceutically acceptable salt thereof. Preferably the compound of Formula I is the compound of Formula II or the compound of Formula III. The combination may be administered simultaneously or separately.

In a further embodiment, the invention provides a pharmaceutical composition comprising a) a compound of Formula I or a pharmaceutically acceptable salt thereof as defined in any one of the first to seventh embodiments; b) one or more additional antidepressants or a pharmaceutically acceptable salt thereof; and c) one or more pharmaceutically acceptable excipients. Preferably the compound of Formula I is the compound of Formula II or the compound of Formula III. Preferably the one or more additional antidepressants is selected from the list hereinabove, more preferably a Serotonin Reuptake Inhibitor (SSRI) or a pharmaceutically acceptable salt thereof; more preferably the SSRI is selected from citalopram, dapoxetine, escitalopram, fluoxetine, fluvoxamine, paroxetine and sertraline, or a pharmaceutically acceptable salt thereof.

Administration of a compound of Formula I, particularly the compound of Formula II or Formula III, or a pharmaceutically acceptable salt thereof, in combination with one or more of the additional antidepressants listed above, may have a number of advantages, such as improved treatment or control of treatment resistant unipolar depressive disorder, reduced dose of the one or more additional active ingredients, reduction in side effects, and improved patient compliance.

Administration of the combinations of the invention may be simultaneous, or separate, and can be provided in the form of a kit comprising the two or more active ingredients, either combined together in a single medicament, or separately in the form of separate medicaments.

In a further embodiment, the invention provides a kit comprising a) a compound of Formula I or a pharmaceutically acceptable salt thereof as defined in any one of the first to seventh embodiments; and b) an additional antidepressant. Preferably the compound of Formula I is the compound of Formula II or the compound of Formula III. Preferably the additional antidepressant is selected from those listed hereinabove. The kit may further comprise c) instructions for administration Experimental $5\text{-HT}_{2A}$ receptor function was modelled in mice by measuring the behavioural (head-twitches) and cortical immediate early gene (IEG; Arc, c-fos and Erg2 mRNA) responses to $5\text{-HT}_{2A}$ receptor agonist administration. Ebselen and lithium were administered either acutely or chronically prior to assessment of $5\text{-HT}_{2A}$ receptor function. Ebselen was also tested for the antidepressant augmenting action associated with reduced $5\text{-HT}_{2A}$ function by co-administration with the SSRI citalopram in microdialysis (extracellular 5-HT) experiments.

Animals

Mice (male C57BL/6, 7-9 weeks; Harlan, Bicester, UK) were housed in groups of 6 under controlled conditions of lighting (12 h light-dark cycle, lights on 08.00 h) and temperature (21±1° C.), with food and water freely available. Experiments were carried out during the light phase. Experiments conformed to the UK Animals (Scientific Procedures) Act 1986 and were approved by local ethical review process and covered by a Home Office Project Licence.

Behavioural Measurements

Central $5\text{-HT}_{2A}$ receptor function was assessed in behavioural studies by measuring involuntary head-twitches (head-twitch response, HTR) evoked by administration of a hallucinogenic non-selective $5\text{-HT}_{2A}$ receptor agonist, DOI or psilocin. Stereotypical scratching of the ear (ear scratch response, ESR) with one or two paws was also measured as this is another $5\text{-HT}_{2A}$ receptor-mediated effect of such agents (Darmani et al., 1990, Pharmacology, biochemistry, and behavior 37: 95-99; Gonzalez-Maeso et al., 2007, Neuron 53: 439-452). The challenge doses of DOI (2 mg kg$^{-1}$ i.p.) and psilocin (2 mg kg$^{-1}$ i.p.) were selected on the basis of prior dose response studies and evidence that DOI-induced HTR was blocked by a selective $5\text{-HT}_{2A}$ receptor antagonist (Jennings et al., 2008, Neuropharmacology 54: 776-783).

Animals were randomly allocated to one of the following treatments (6-13 mice per group): i) acute ebselen (1, 5 or 10 mg kg$^{-1}$ i.p.) or vehicle; ii) repeated ebselen (10 mg kg$^{-1}$ i.p., twice daily for 7 days, last injection morning of the 8$^{th}$ day) or vehicle; iii) acute lithium (10 mmol kg$^{-1}$ i.p.) or vehicle; and iv) repeated lithium (3 days; 10 mmol kg$^{-1}$ i.p. on day 1, 3 mmol kg$^{-1}$ i.p. twice daily on days 2-3: 7 days; 10 mmol kg$^{-1}$ i.p. on day 1, 3 mmol kg$^{-1}$ i.p. twice daily on days 2-7) or vehicle. These drug doses and pre-treatment times were selected according to optimal times reported in previous studies; ebselen (1 h; Nature communications 4: 1332), and lithium (5 or 18 h; (Goodwin et al., 1986, Psychopharmacology 90: 482-487).

Mice were placed individually in transparent, plexiglass chambers 1 h before administration of DOI (2 mg kg$^{-1}$ i.p.) or psilocin (2 mg kg$^{-1}$ i.p.). Behaviour was monitored by an overhead video camera and the number of head-twitches and ear scratches was scored (5 min after agonist injection, for 15 min) offline by an observer blind to treatment.

Measurement of IEG Expression

In separate molecular studies, central $5\text{-HT}_{2A}$ receptor function was assessed by measuring DOI-induced mRNA expression of the IEG c-fos, as well as complementary IEGs Arc and egr2 in cortical regions (Gonzalez-Maeso et al., 2007; Jennings et al., 2008). The challenge dose of DOI (2 mg kg$^{-1}$ i.p.) was selected on the basis of preliminary dose response studies and evidence that DOI-evoked IEG expression was blocked by a selective $5\text{-HT}_{2A}$ receptor antagonist (Jennings et al., 2008).

Mice were randomly allocated to one of the following treatments (6 mice per group); i) acute ebselen (10 mg kg$^{-1}$ i.p.) or vehicle, ii) repeated lithium (3 days; 10 mmol kg$^{-1}$ i.p. on day 1, 3 mmol kg$^{-1}$ i.p. twice daily on days 2-3) or vehicle. Drug doses and pre-treatment times were selected as noted above; ebselen (1 h), lithium (18 h). Groups of mice were acclimatised to a procedure room for 4 h prior to each experiment. One h following administration of DOI (2 mg kg$^{-1}$ i.p.), mice were culled by cervical dislocation, and brains were dissected, snap frozen in isopentane on dry ice, and stored in −80° C.

c-Fos, Arc and egr2 mRNA was measured on tissue sections using in situ hybridization (Jennings et al., 2008). Coronal sections (12 μm) were cryostat cut and collected on gelatinised slides. Sections were stored in −80° C. prior to pre-treatment with paraformaldehyde- and triethanolamine/acetic acid-based solutions and dehydration with increasing concentrations of alcohol solutions. Slides were then allowed to air-dry overnight and stored in −20° C.

Oligonucleotide probes complementary to c-fos (CTTCAGGGTAGGTGAAGACAAAGG-AA-GACGTGTAAGTAGTGCAGC), Arc (CTCGGTTGCC-CATCCTCACCTGGCCCCCAAG-ACTGATATTGCTGA) and egr2 (GATCATAGGAATGAGACCTGGGTCCAT-AGCTGG-CTTGG) mRNA were 3'-tail labelled with [$^{35}$S]-ATP (Hartmann Analytic GmbH, Germany). For hybridisation, sections were defrosted, cover-slipped, and incubated at 34° C. for 16 h with a hybridization mix (consisting of the radiolabelled oligonucleotide (2.4×10$^6$ cpm/section), 50 mM dithiothreitol and hybridization buffer (50% deionised formamide, 4× saline sodium citrate (SSC), 25 mM sodium phosphate buffer, 1 mM sodium pyrophosphate, 5× Denhart's solution, 0.2 μg ml$^{-1}$ boiled herring sperm, 0.1 mg ml$^{-1}$ polyadenylic acid, 120 μg ml$^{-1}$ heparin, 0.1 g ml$^{-1}$ dextran powder). Cover slips were then removed and sections were washed with 1×SSC, 50° C. for 20 min. Washes were repeated twice followed by 2×60 min washes at room temperature with 1×SSC. Sections were then immersed in double deionised water and dried overnight before being placed in cassettes and exposed to autoradiographic film (Kodak BioMax MR) for 7 days. Autoradiographic films were developed using an automatic X-ray film processor (Compact X4, X-ograph). Controls included using the sense orientation of the oligonucleotide and displacement with unlabelled probes.

Optical density measurements were obtained from the autoradiograms using computer-based image analysis (MCID software). Optical density readings were converted in nCi g$^{-1}$ of tissue by calibration with the use of [$^{14}$C] microscales, which were co-exposed with the slides. Measurements of regions of interest were taken bilaterally from 3 sections per slide and the values for each region of interest were averaged.

Receptor Autoradiography

The effect of ebselen and lithium treatment on the abundance of cortical 5-HT$_{2A}$ receptor binding sites was measured using receptor autoradiography. Mice were randomly allocated to one of the following treatments (6 mice per group); i) acute ebselen (10 mg kg$^{-1}$ i.p.) or vehicle, ii) repeated ebselen (10 mg kg$^{-1}$ i.p., twice daily for 7 days; last injection morning of the 8$^{th}$ day) or vehicle, and iii) repeated lithium (7 days; 10 mmol kg$^{-1}$ i.p. on day 1, 3 mmol kg$^{-1}$ i.p. twice daily on days 2-7) or vehicle.

Tissue sections (12 μm) were cryostat-cut at the level of the frontal cortex and stored in −80° C. On the day of the experiment, sections were incubated (at room temperature) in Tris-HCl buffer (0.17 M, pH 7.7) for 20 min, and then for 2 h with either 2 nM [$^3$H]-ketanserin (PerkinElmer) to determine total binding, or 2 nM [$^3$H]-ketanserin plus 10 μM methysergide to determine non-specific binding. Sections were then washed twice for 10 min with ice-cold 4° C. Tris-HCl buffer (0.17 M, pH 7.7), followed by double deionised water. Finally, slides were air-dried overnight before being exposed to autoradiographic films (BioMax MR, Kodak) for 12 weeks.

Optical density measurements were obtained from the autoradiograms as described above. Measurements were taken bilaterally, from three sections per slide, and values were averaged. Specific binding was calculated by subtracting non-specific binding from total binding. Optical density measurements were calibrated using $^3$H-microscales that were co-exposed with the sections, and converted to values of nCi g$^{-1}$ tissue.

Microdialysis

Mice (4-8 per group) were stably anaesthetised with isoflurane (2%, delivered in oxygen) and body temperature was maintained at 36±1° C. using a homeothermic blanket attached to a rectal probe. After mounting in a stereotaxic frame (Kopf) a hole was drilled over the hippocampus and a guide cannula (5 mm length, 0.2 mm outer diameter; Royem Scientific Ltd) was stereotaxically lowered into the hippocampus (coordinates from bregma: AP −3.0, ML −3.3, DV −4.4 atlas of (Paxinos, 2007) and secured with dental cement. Mice were then removed from the frame and allowed to recover for 6-7 days.

On the day of the experiment, mice were briefly anaesthetised with isoflurane and a microdialysis probe (7 mm length, 2 mm 6 KDa PES membrane; Royem Scientific Ltd) was slowly lowered through the guide cannula, into hippocampus. The microdialysis probe was connected to a perfusion pump (CMA/100, CMA Microdialysis Ltd.) and perfused (2 μl min$^{-1}$) continuously with artificial CSF (140 mM NaCl, 3 mM KCl, 1.2 mM Na$_2$HPO$_4$, 0.27 mM NaH$_2$PO$_4$, 1 mM MgCl$_2$, 2.4 mM CaCl$_2$ and 7.2 mM glucose). After 2 h perfusate samples were collected every 20 min and analysed immediately by HPLC with electrochemical detection (see below).

Once 3 consecutive baseline samples were stable, mice received a single injection of ebselen (10 mg kg$^{-1}$ i.p.) or vehicle. Citalopram (5 mg kg$^{-1}$ i.p.) was administered 1 h later and dialysates were collected for a further 2 h. At the end of each experiment, brains were removed and probe placement was confirmed by histological examination.

Measurement of 5-HT Synthesis and Tissue Levels of 5-HT, 5-HIAA and Tryptophan

The level of 5-HT synthesis in frontal cortex and hippocampus was obtained by measuring the accumulation of 5-HTP following inhibition of aromatic amino acid decarboxylase. Mice (n=6 per group) were administered ebselen (0.5, 1 or 5 mg kg$^{-1}$ i.p.) or vehicle and 1 h later animals were injected with the aromatic amino acid decarboxylase inhibitor NSD1015 (100 mg kg$^{-1}$ i.p.). Mice were then culled by cervical dislocation 30 min following NSD1015 and brain tissue was removed and stored at −80° C. Separate experiments measured levels of 5-HT, 5-HIAA and tryptophan in cortex and hippocampus. Mice (n=6 per group) were administered ebselen (0.5, 1 or 5 mg kg$^{-1}$ i.p.) or vehicle and then culled by cervical dislocation 1 h post-drug. Brain tissue was dissected out and stored at −80° C. prior to neurochemical analysis.

On the day of neurochemical analysis, tissue pieces (~20 mg) of frozen frontal cortex and hippocampus were placed in Eppendorf tubes containing 500 μl perchloric acid (0.09 M) and homogenised using a polytron kinetic homogeniser (15000 rpm for 10 sec). Tissue homogenates were then centrifuged (1000 rpm for 10 min) and the supernatant was transferred in a new Eppendorf tube, protected from light, and kept on ice before analysis using HPLC with electrochemical detection (see below).

HPLC with Electrochemical Detection

Both mcrodialysates (20 μl) and brain tissue supernatants (50 μl) were analysed by an HPLC system, comprising a silica-based, reversed phase column (3.0 µm ODS2, 4.6 mm×100 mm, Waters Ltd) coupled to an electrochemical detector (glass carbon working electrode versus Ag/AgCl reference; LC-4C, Bioanalytical systems). For microdialysates, analytes were separated at room temperature by an isocratic mobile phase comprising 12.5% (v/v) methanol, 0.13 M $NaHPO_4.H_2O$, 0.025 mM octane sulphonic acid, 0.85 mM EDTA and 2 mM NaCl at pH 3.5, and with the working electrode set at +0.7 V.

For measurement of 5-HT, 5-HIAA and tryptophan in brain tissue supernatants, analytes were separated at room temperature by an isocratic mobile phase comprising an isocratic mix of 15% (v/v) methanol, 2 mM 1-octanesulphonic acid, 0.12 M $NaHPO_4.H_2O$, 2 mM NaCl, and 0.1 mM EDTA at pH 3.7 with the working electrode set at +0.85V. For measurement of 5-HTP the mobile phase was adjusted to pH 3.4.

Drugs

Drugs were obtained from the following suppliers (in brackets); DOI (1-(2,5-dimethoxy-4-iodophenyl)-propan-2-amine; Tocris, U.K.), ebselen (2-phenyl-1,2-benzisoselenazol-3(2H)-one; Sigma), lithium chloride (MP biomedicals LLC), psilocin (3-[2-(dimethylamino)ethyl]-4-indolol; LGC standards), L-690,330 ([1-(4-hydroxyphenoxy) ethylidene] bisphosphonic acid; Tocris), AR-A014418 (N-[(4-methoxyphenyl)methyl]-N'-(5-nitro-2-thiazolyl) urea; Tocris), NSD1015 (3-hydroxybenzylhydrazine dihydrochloride; Sigma) and citalopram (Tocris). Drugs were dissolved in saline (DOI, lithium, L-690,330, NSD1015), 4% (2-hydroxypropyl)-β-cyclodextrin with 0.4% (v/v) dimethyl sulfoxide (ebselen) or 0.05 mM tartaric acid, pH 6-7 (psilocin). Volume of injection was either 0.01 (DOI, psilocin, L-690,330, lithium, NSD1015, citalopram) or 0.02 (ebselen, AR-A 014418) ml $g^{-1}$ body weight.

Data Analysis

Data are expressed as % of controls and given as mean±SEM values. Data were analysed statistically using IBM SPSS Statistics (version 20) and differences were considered statistically significant when p<0.05. For behavioural data, the effect of treatment was compared to vehicle using Student's unpaired t-test or one-way ANOVA followed by the LSD post-hoc test, as appropriate. For gene expression data, the effect of treatment was compared to vehicle using one-way ANOVA followed by LSD post-hoc test for selected comparisons, with each region being considered an independent variable. For the receptor autoradiography data, the effect of treatment on [$^3$H]-ketanserin binding was compared to vehicle using Student's unpaired t-test. The tissue neurochemical measurements were analysed by a one-way ANOVA followed by Dunnett's test for multiple comparisons with the vehicle injected control group. The microdialysis data were analysed by one-way ANOVA, followed by LSD post-hoc.

Results

Effect of Ebselen on DOI-Evoked Behavioural Responses

Figure 1B:
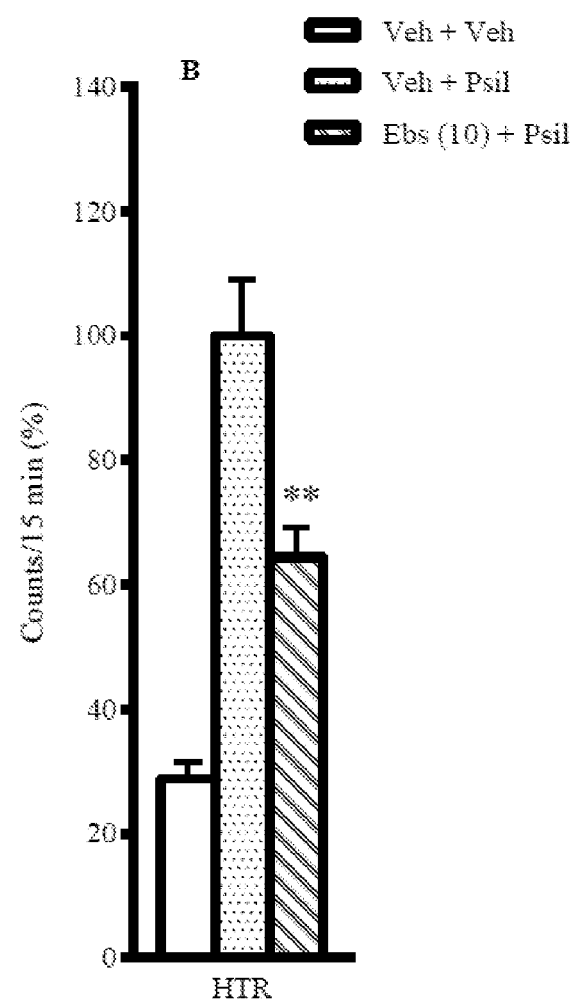
Figure 1C:
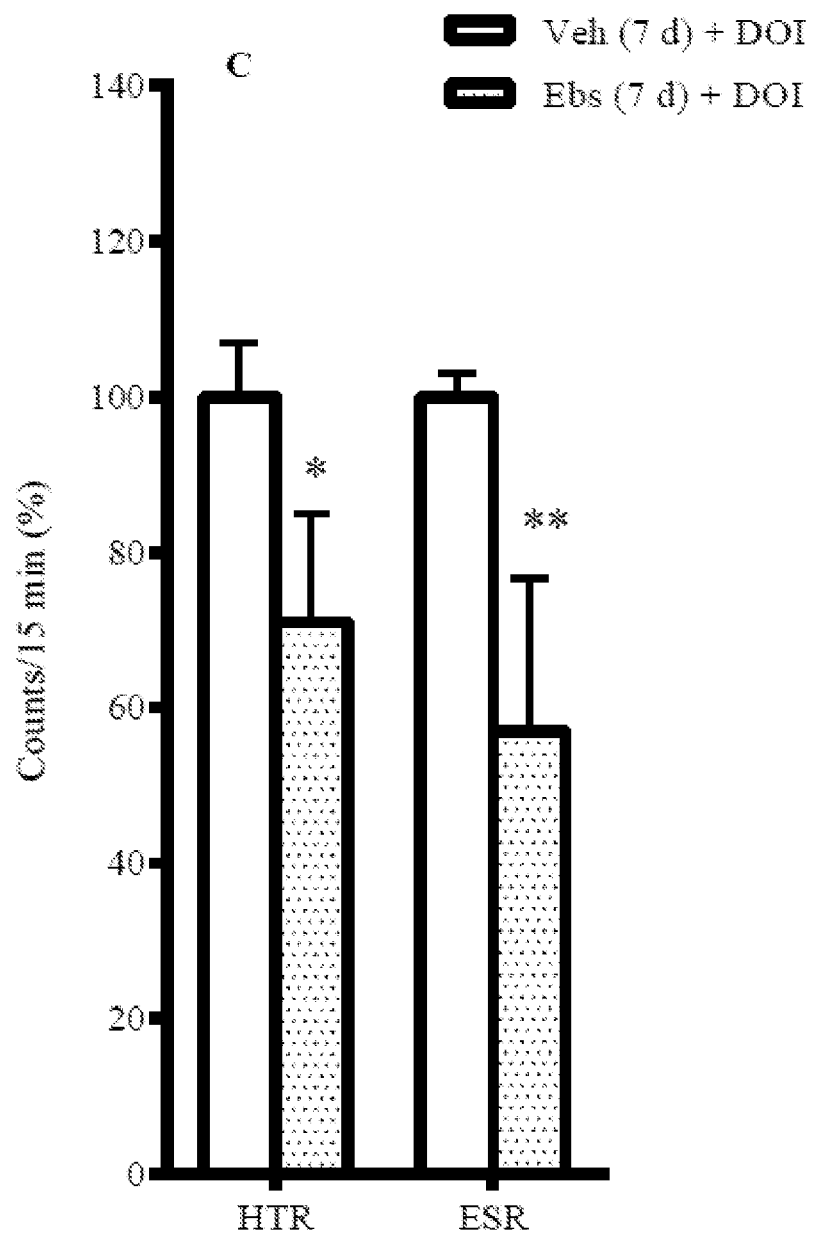

Administration of the 5-$HT_{2A}$ receptor agonist DOI (2 mg $kg^{-1}$ i.p.) evoked both a HTR and ESR compared to injection of vehicle, which had little effect alone (FIG. 1A). Pretreatment with ebselen (1, 5 or 10 mg $kg^{-1}$) caused a dose-related decrease in the DOI-evoked HTR and ESR that was statistically significant when compared to DOI alone, although ebselen did not completely block these effects of DOI (FIG. 1A). The non-selective 5-$HT_{2A}$ receptor agonist psilocin (2 mg $kg^{-1}$ i.p.) also induced a HTR compared to vehicle controls and this effect was also decreased by ebselen (FIG. 1B). The inhibitory effect of ebselen on the HTR and ESR evoked by DOI persisted in mice treated repeatedly with ebselen (10 mg $kg^{-1}$ i.p. for 7 days) (FIG. 1C).

Effect of Lithium on DOI-Evoked Behavioural Responses

Figure 2A:
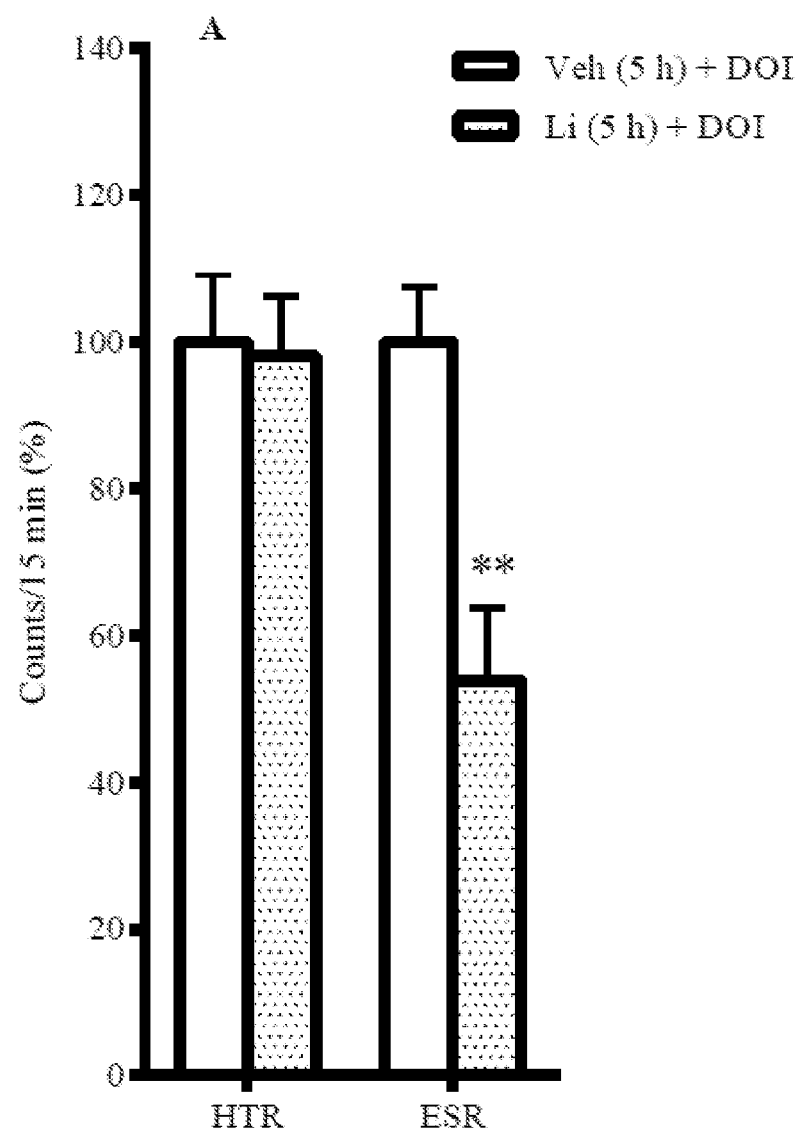
FIG. 2 shows the effect of lithium on DOI-evoked behavioural responses.
Figure 2B:
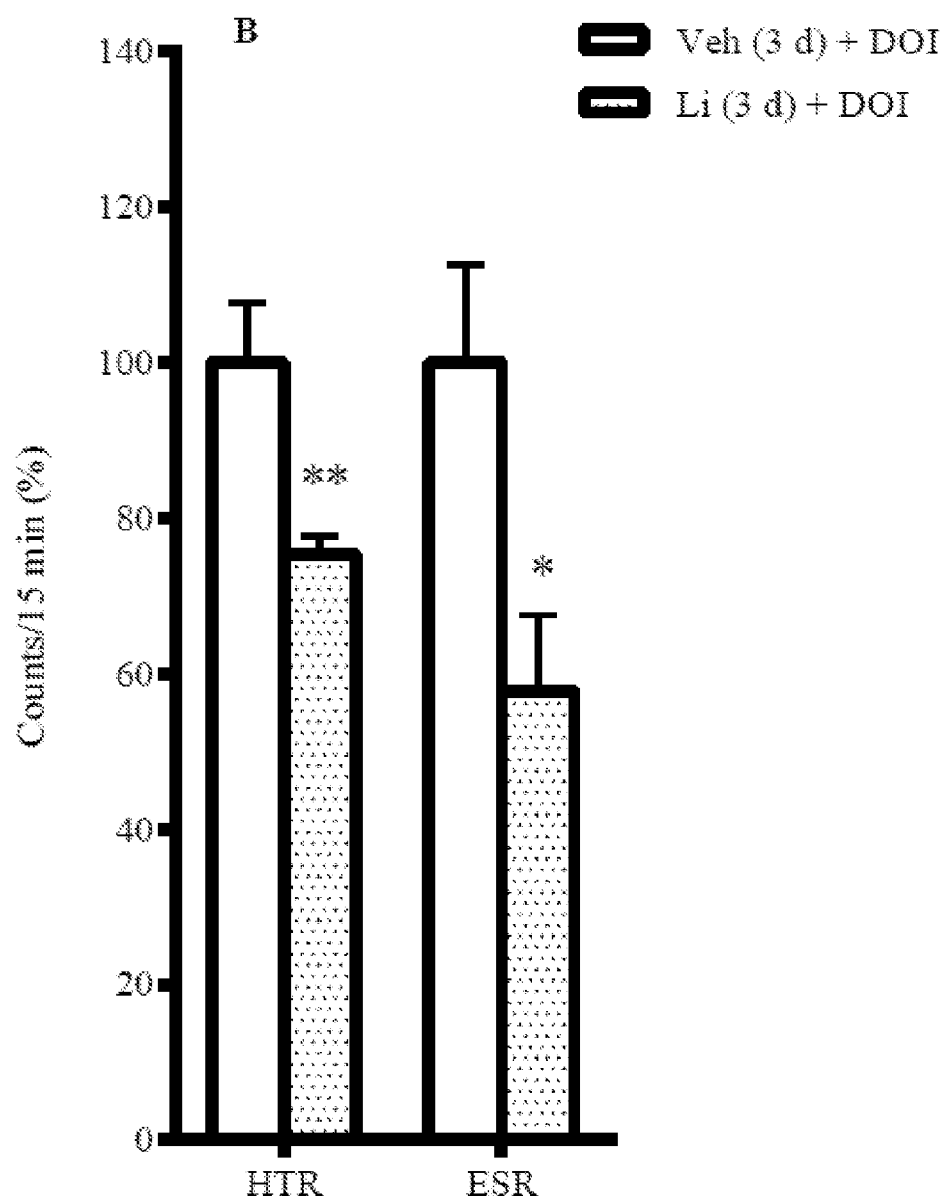
Figure 2C:
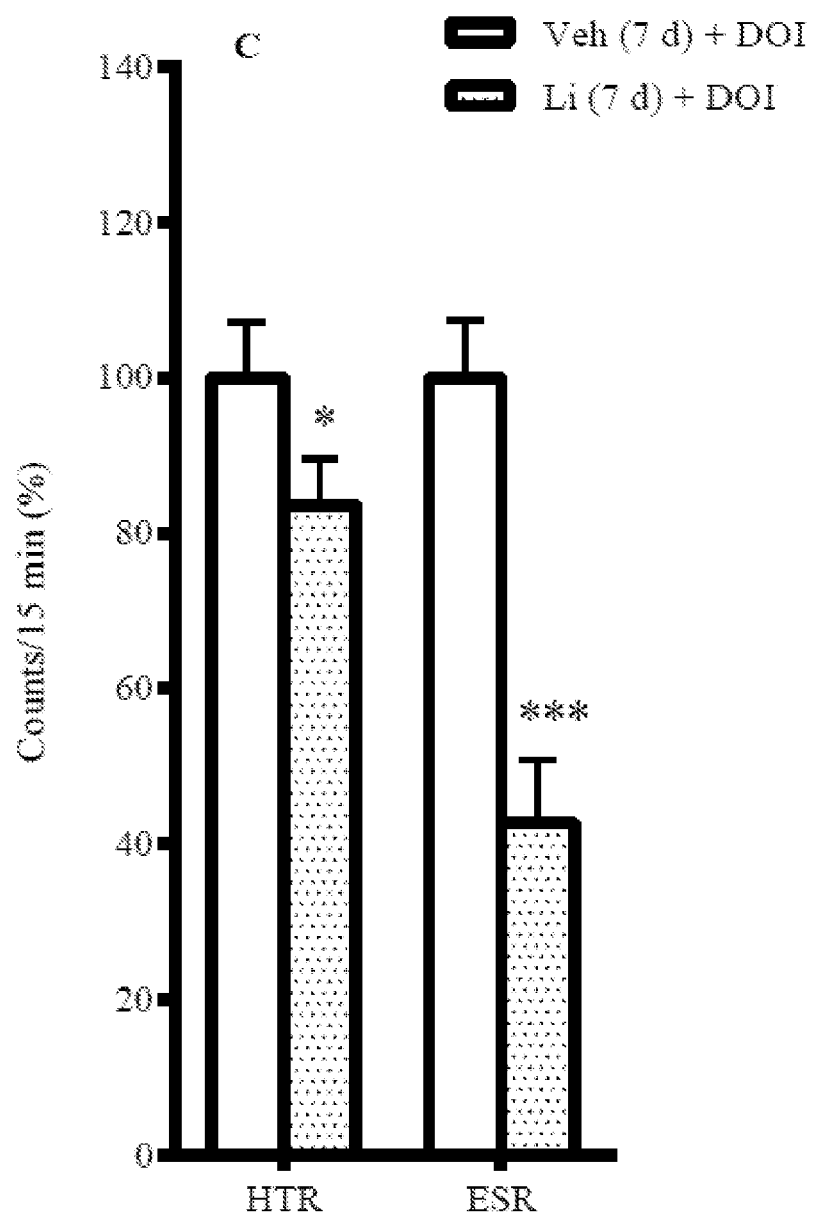

The inhibitory effect of ebselen on the HTR and ESR to DOI was compared with that of lithium. Compared to the effect of DOI alone, acute administration of lithium (10 mmol $kg^{-1}$ i.p.) reduced the ESR to DOI but the HTR was not significantly changed (FIG. 2A). However, repeated administration of lithium for 3 days (10 mmol $kg^{-1}$ i.p. day 1, 3 mmol $kg^{-1}$ i.p. days 2-3) decreased both the HTR and ESR to DOI (FIG. 2B). When administered repeatedly for 7 days (10 mmol $kg^{-1}$ i.p. day 1, 3 mmol $kg^{-1}$ i.p. days 2-7) lithium was similarly effective in reducing the DOI-evoked HTR and ESR compared to vehicle controls (FIG. 2C).

Effect of IMPase and GSK-3 Inhibitors on DOI-Evoked Behavioural Responses

Figure 3A:
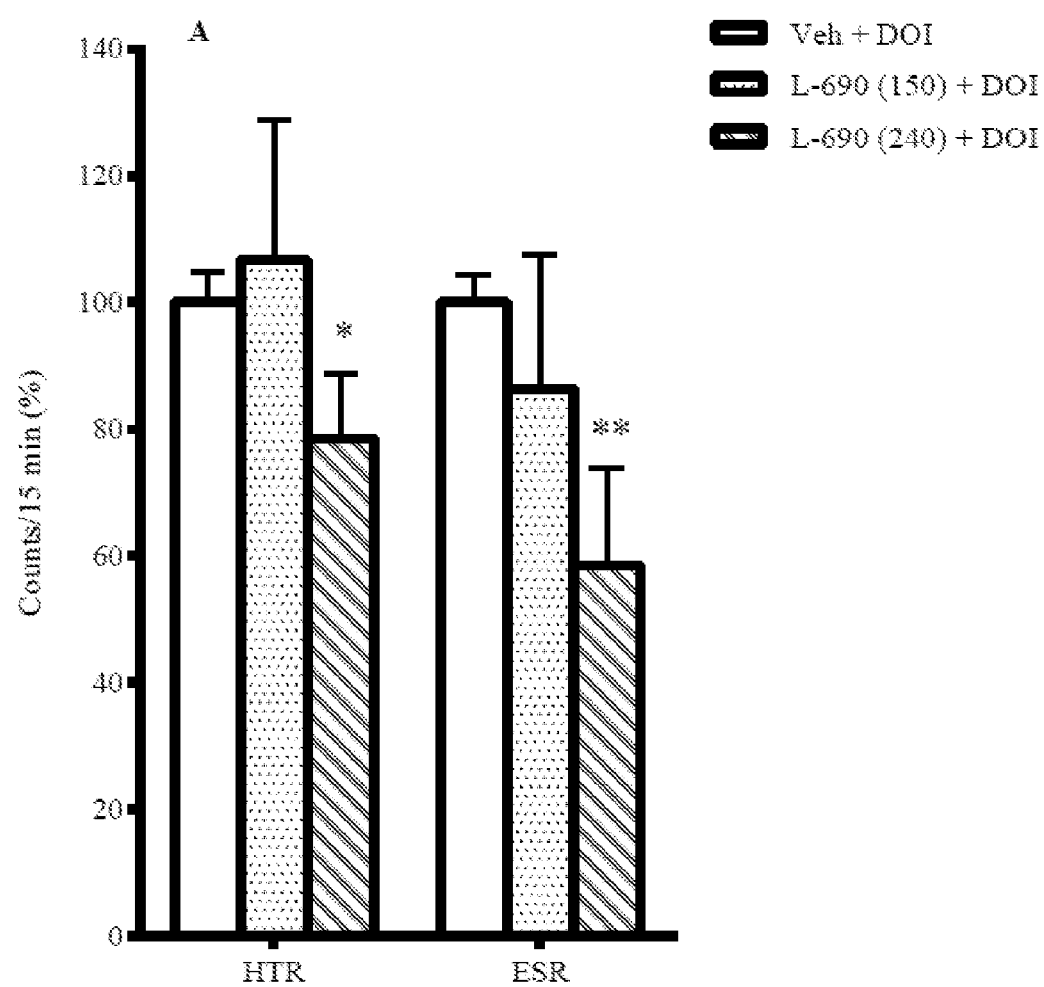
FIG. 3 shows the effect of IMPase and GSK-3 inhibitors on DOI-evoked behavioural responses.
Figure 3B:
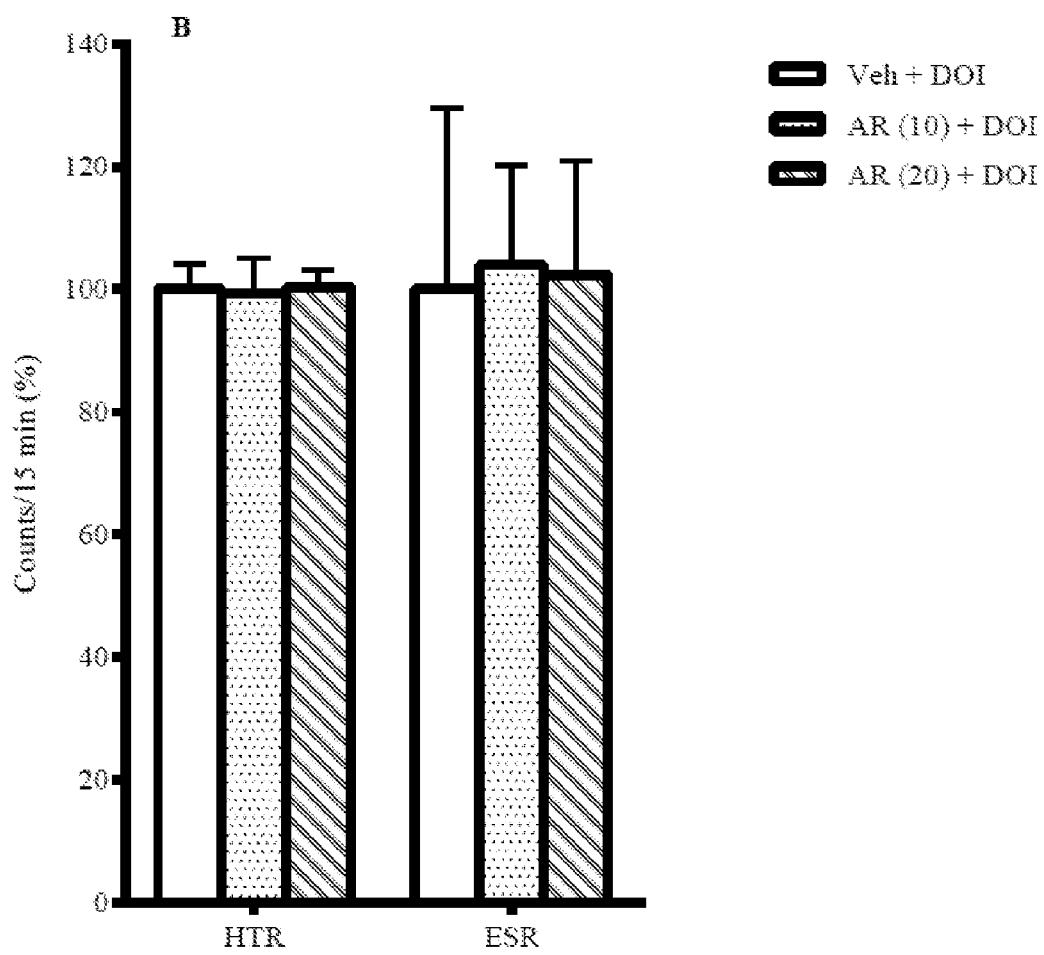

To test whether IMPase inhibition might be involved in the inhibitory effect of ebselen and lithium on the behavioural measures of 5-$HT_{2A}$ receptor function, the IMPase inhibitor, L-690,330 was tested. Pretreatment with L-690,330 (150 or 240 mg $kg^{-1}$ i.p.) decreased both the HTR and ESR to DOI compared to the effect of DOI alone (FIG. 3A). Inhibition of GSK-3 is also a potential mediator of the actions of ebselen and lithium, however pretreatment with the GSK-3 inhibitor AR-A014418 (10 or 20 mg $kg^{-1}$ i.p.) did not affect the DOI-induced HTR and ESR (FIG. 3B).

Effect of Ebselen on DOI-Evoked IEG Responses

Figure 4A:
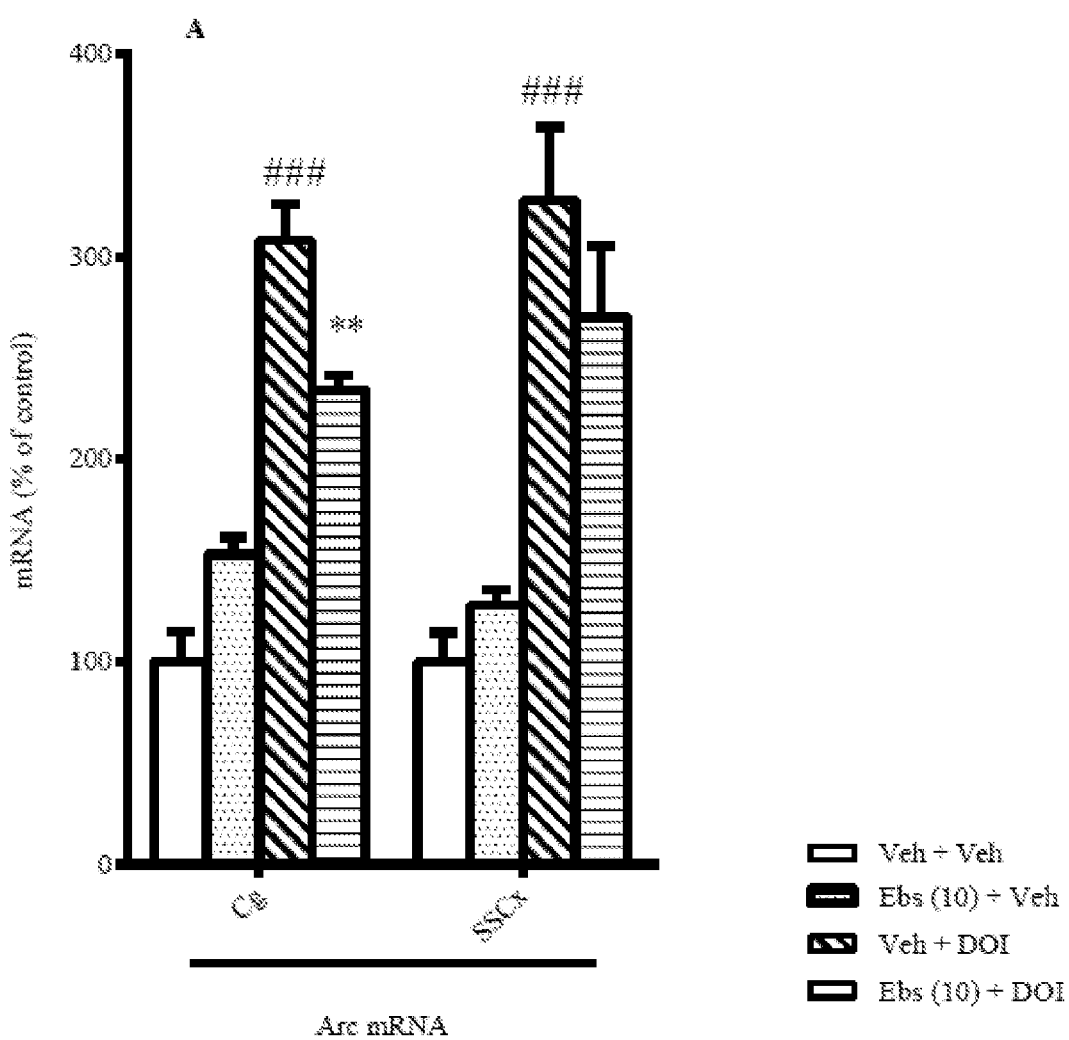
FIG. 4 shows the effect of ebselen on DOI-evoked IEG responses.
Figure 4B:
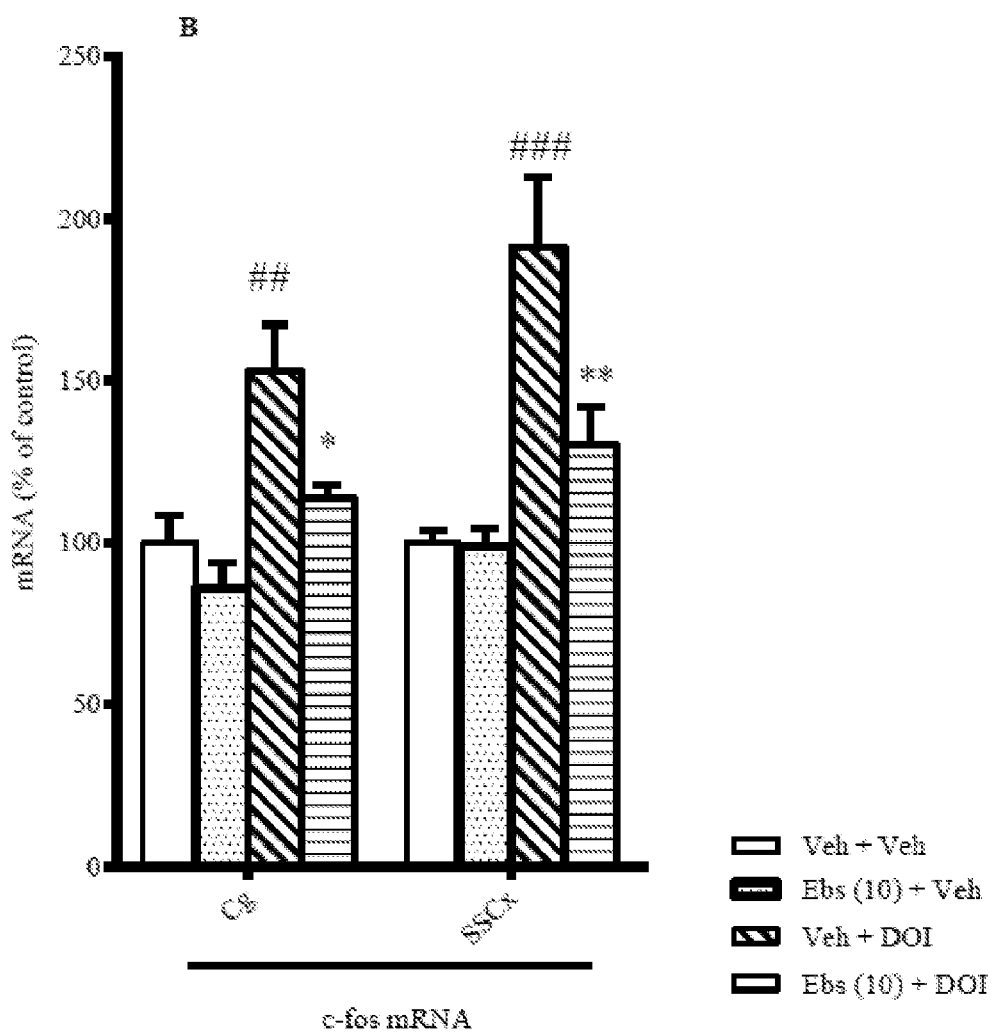
Figure 4C:
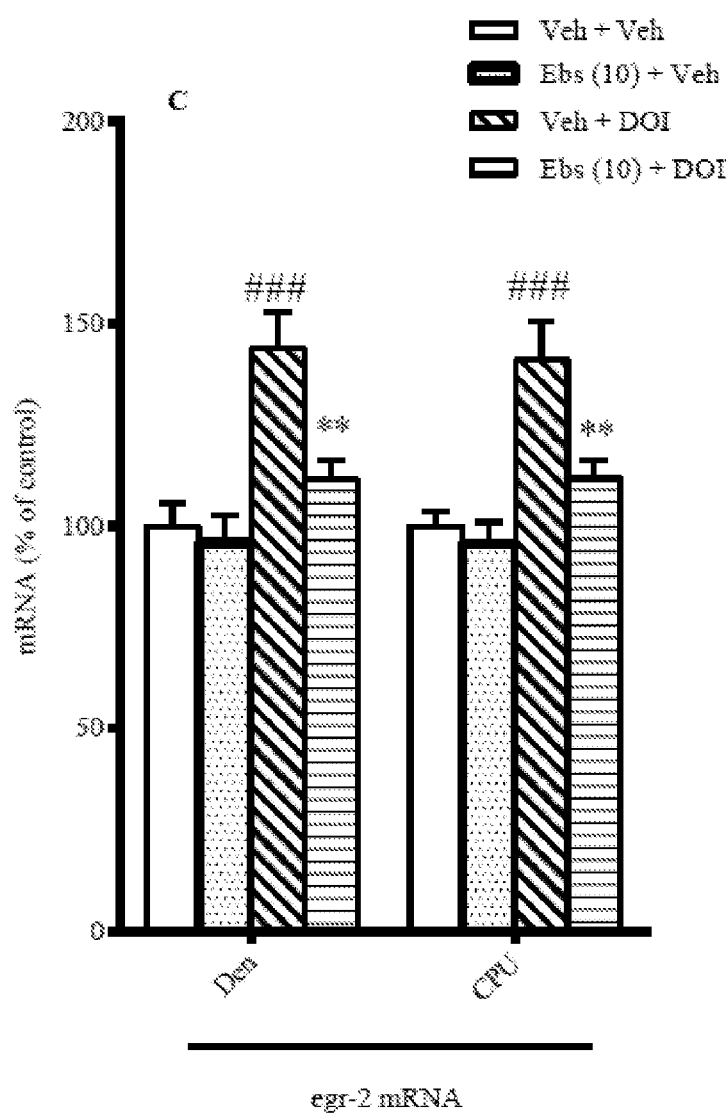

Experiments tested whether the effect of ebselen on the behavioural measurement of 5-$HT_{2A}$ receptor function could be confirmed by molecular measurement using IEG expression. DOI (2 mg $kg^{-1}$ i.p.) induced a marked increase in mRNA abundance of the IEGs c-fos, Arc and egr2, and this effect was apparent across various brain regions. Quantification of IEG mRNA in selected regions (cingulate and somatosensory cortices for c-fos and Arc, caudate nucleus and endopiriform cortex for egr-2) revealed that DOI evoked increases in IEG mRNA of approximately 50-200% above vehicle-injected controls (FIG. 4 A-C). Pretreatment with ebselen (10 mg $kg^{-1}$ i.p.) attenuated these IEG responses to DOI. This effect of ebselen was apparent in both cingulate and somatosensory cortex for Arc (FIG. 4A) and c-fos (FIG. 4B), and in the caudate nucleus and endopiriform cortex for egr-2 (FIG. 4C).

Effect of Lithium on DOI-Evoked IEG Responses

Figure 5A:
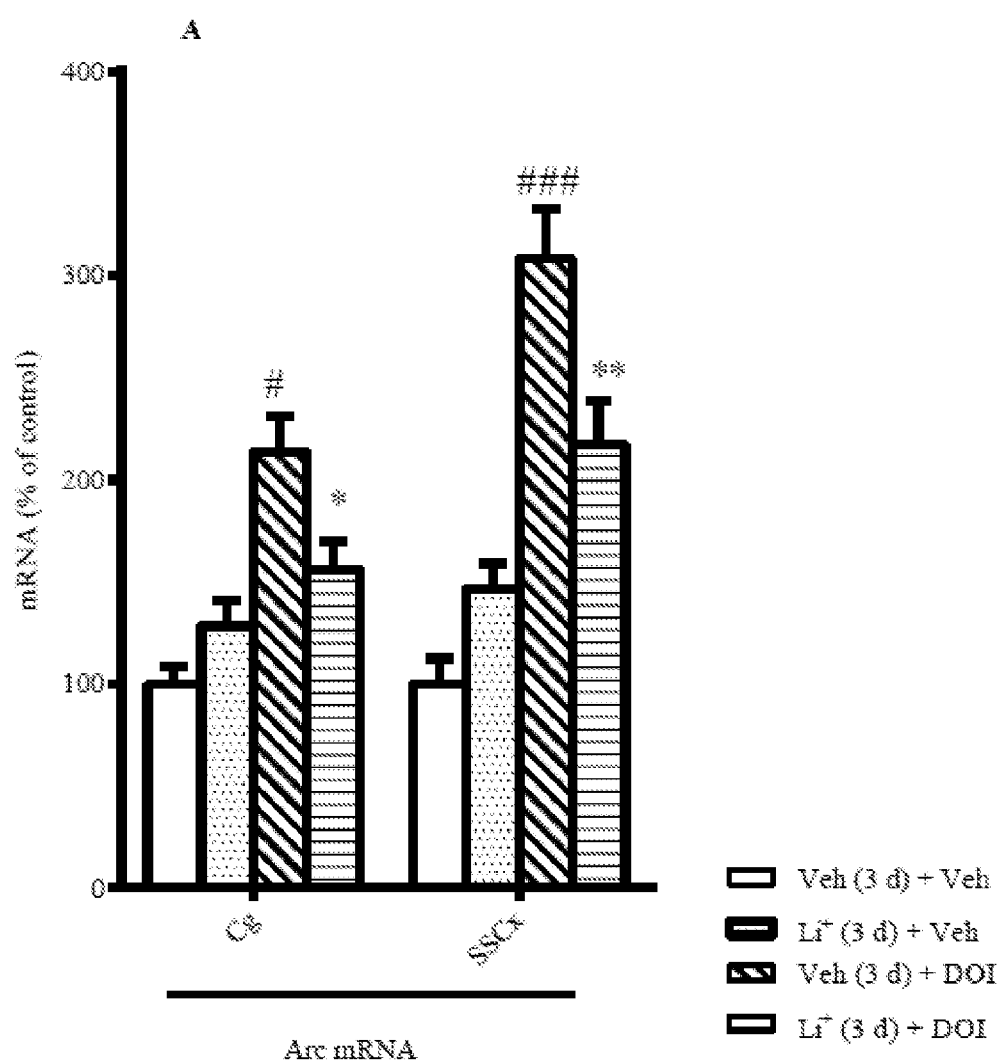
FIG. 5 shows the effect of lithium on DOI-evoked IEG responses.
Figure 5B:
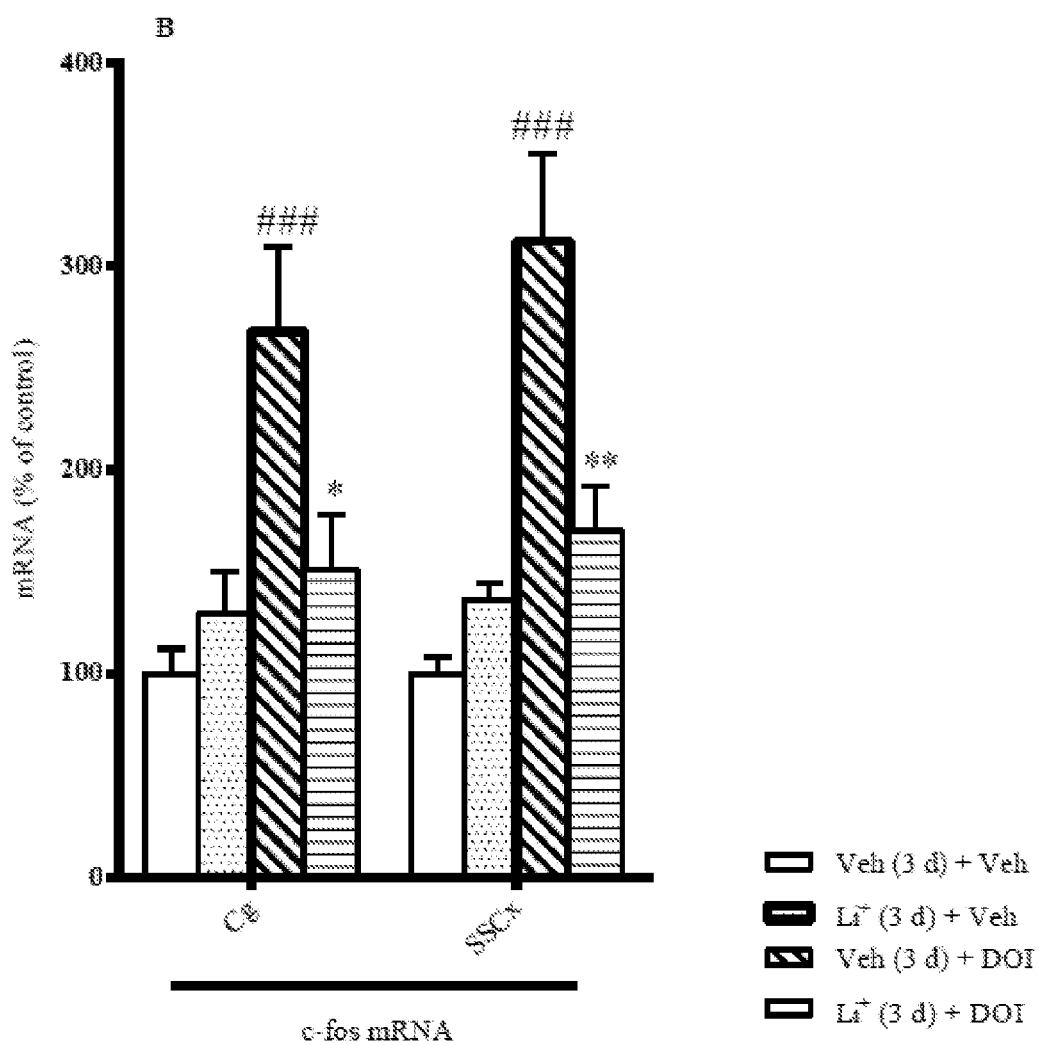
Figure 5C:
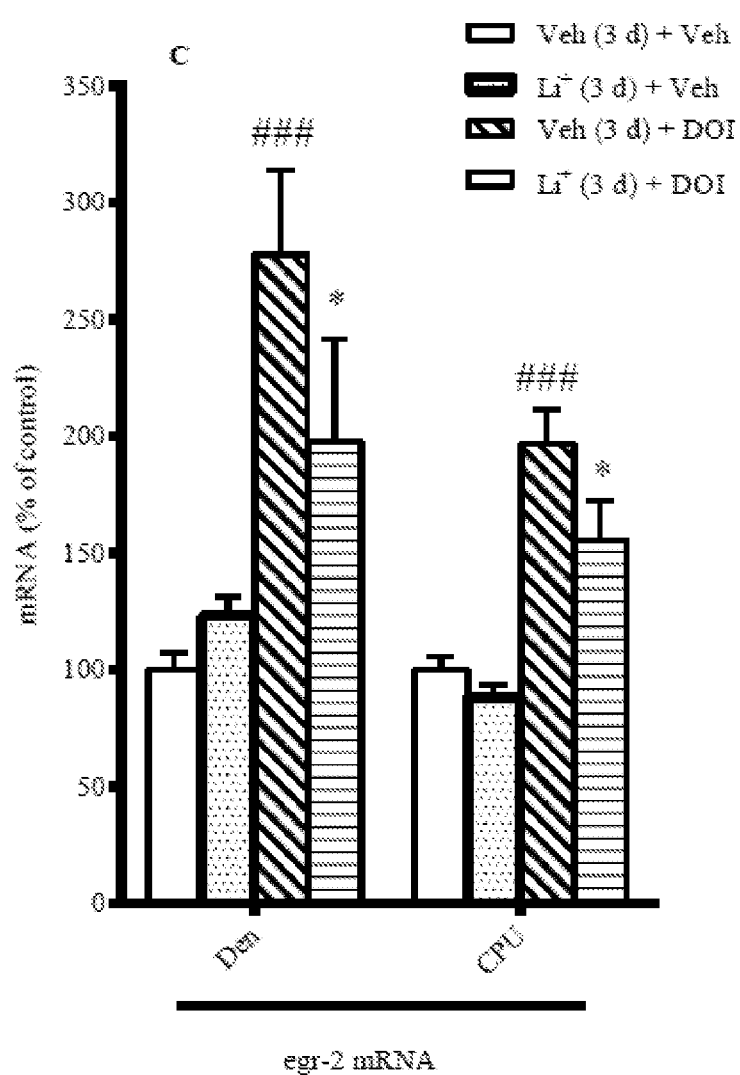

Experiments also tested whether lithium reduced 5-$HT_{2A}$ receptor function in the IEG expression model. As with ebselen, pretreatment with lithium (3 days, 10 mmol $kg^{-1}$ i.p. day 1, 3 mmol $kg^{-1}$ i.p. days 2-3) attenuated the IEG responses to DOI. This effect of lithium was detected in both cingulate and somatosensory cortex for Arc (FIG. 5A) and c-fos (FIG. 5B), and in the caudate nucleus and endopiriform cortex for egr-2 (FIG. 5C).

Effect of Ebselen and Lithium on 5-$HT_{2A}$ Receptor Binding Sites

Experiments using the inhibitor of IMPase suggested that the decrease in 5-$HT_{2A}$ receptor function by ebselen and lithium may be mediated by disruption of 5-$HT_{2A}$ receptor signalling, but a down-regulation of 5-$HT_{2A}$ receptor expression is an alternative explanation. To test this possibility, 5-$HT_{2A}$ receptor binding was measured in mice treated with ebselen or lithium at doses and durations that reduced 5-$HT_{2A}$ receptor function. Receptor autoradiography demonstrated the expected high abundance of [$^3$H]-ketanserin binding sites in mouse frontal cortex. In mice administered an acute dose of ebselen (10 mg $kg^{-1}$ i.p.) there was a slight decrease in [$^3$H]-ketanserin binding sites but this was not statistically significant compared to vehicle controls (Table 1). In comparison, repeated administration of ebselen (10 mg kg$^{-1}$ i.p. for 7 days) had no effect on the abundance [$^3$H]-ketanserin binding sites compared to vehicle-injected controls (Table 1). Similarly, the abundance of [$^3$H]-ketanserin binding sites was not altered by repeated administration of lithium (7 days, 10 mmol kg$^{-1}$ i.p. day 1, 3 mmol kg$^{-1}$ i.p. days 2-7).

TABLE 1

Effect of ebselen on 5-HT$_{2A}$ receptor binding sites in mouse frontal cortex.

| Treatment | [$^3$H]-Ketanserin (nCi g$^{-1}$ of tissue) |
|---|---|
| Vehicle | 4.33 ± 0.66 |
| Ebselen (2h) | 3.36 ± 0.38 |
| Vehicle | 6.60 ± 0.27 |
| Ebselen (7 days) | 6.12 ± 0.63 |
| Vehicle | 5.60 ± 0.63 |
| Lithium (7 days) | 5.43 ± 1.30 |

Data shown are mean ± SEM values, n = 6.

Effect of Ebselen in Combination with an SSRI on Brain Extracellular 5-HT

Figure 6:
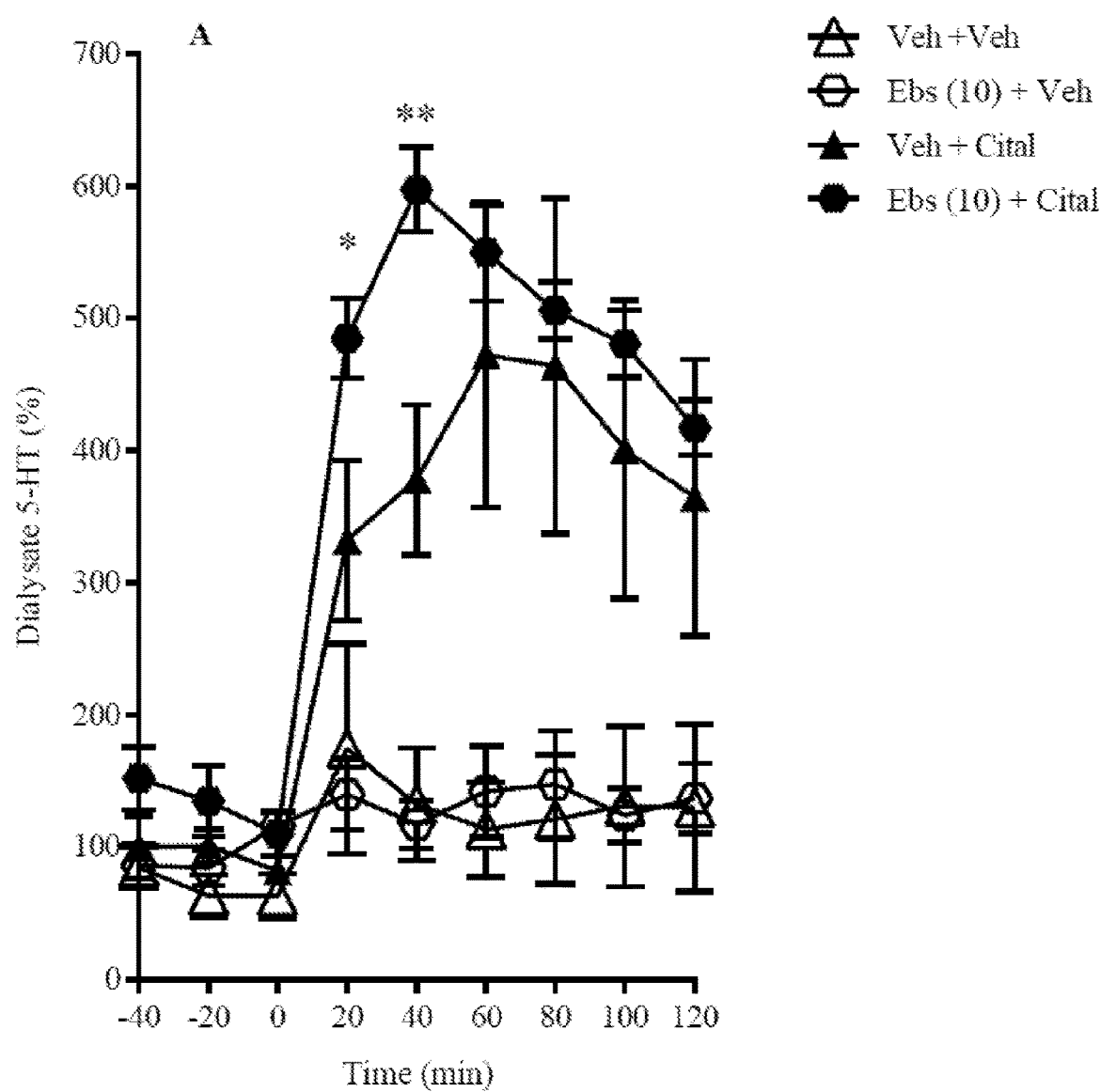
FIG. 6 shows the effect of ebselen in combination with citalopram on brain extracellular 5-HT.

Previous microdialysis studies demonstrate that 5-HT$_{2A}$ receptor blockade augments the effect of an SSRI on brain extracellular 5-HT (Boothman et al., 2006, Neuropharmacology 50: 726-732). Microdialysis experiments tested whether ebselen would similarly enhance the effect of an SSRI. In awake mice, administration of the SSRI citalopram (5 mg kg$^{-1}$ i.p.) increased levels of 5-HT in hippocampal microdialysates, an effect that peaked at approximately 450% above pre-drug values 60 min post injection (FIG. 6). This effect of citalopram was enhanced in mice pretreated with ebselen (10 mg kg$^{-1}$ i.p.), with the greatest effect being 20-40 min post injection of citalopram (FIG. 6). Ebselen alone had no effect on extracellular 5-HT compared to vehicle-injected controls.

Effect of Ebselen on 5-HT Synthesis and Tissue Levels of 5-HT, 5-HIAA and Tryptophan Given the SSRI-augmenting effect of ebselen detected in the above, a final series of experiments tested the effect of different doses of ebselen (0.5, 1 and 5 mg kg$^{-1}$) on various ex vivo neurochemical measures of presynaptic 5-HT function. In the 5-HTP accumulation model of 5-HT synthesis, 5-HTP levels in cortex and hippocampus were greater in mice administered ebselen compared to vehicle controls (Table 2). This increase in 5-HTP was apparent at the highest dose tested (5 mg kg$^{-1}$) but not at lower doses.

In separate experiments, ebselen caused an increase in tissue levels of 5-HT in both cortex and hippocampus compared to vehicle-injected controls, and this effect was observed at all doses tested (0.5, 1 and 5 mg kg$^{-1}$; Table 2). In comparison, 5-HIAA levels in the cortex and hippocampus of these ebselen-treated mice were not significantly different from vehicle controls. One possible explanation for increased 5-HT synthesis and 5-HT levels is increased availability of tryptophan. On the whole, tryptophan levels were slightly higher in ebselen-versus vehicle-treated control mice. However, this effect only reached statistical significance in one region (hippocampus) and at one dose of ebselen (0.5 mg kg$^{-1}$).

TABLE 2

Effect of ebselen on 5-HT synthesis and tissue levels of 5-HT, 5-HIAA and tryptophan in mouse frontal cortex and hippocampus.

| | 5-HTP (% of vehicle) | | 5-HT (% of vehicle) | |
|---|---|---|---|---|
| Treatment | Cortex | Hippocampus | Cortex | Hippocampus |
| Vehicle | 100.0 ± 12.4 | 100.0 ± 9.9 | 100.0 ± 10.6 | 100.0 ± 8.0 |
| Ebselen (0.5 mg kg$^{-1}$) | 109.7 ± 10.6 | 87.9 ± 14.6 | 158.1 ± 14.7*** | 234.4 ± 23.9** |
| Ebselen (1 mg kg$^{-1}$) | 100.4 ± 3.7 | 95.6 ± 6.5 | 148.6 ± 11.2** | 225.9 ± 14.3** |
| Ebselen (5 mg kg$^{-1}$) | 202.5 ± 15.0** | 152.6 ± 9.0* | 130.9 ± 4.8* | 189.4 ± 21.4 |

| | 5-HIAA (% of vehicle) | | Tryptophan (% of vehicle) | |
|---|---|---|---|---|
| Treatment | Cortex | Hippocampus | Cortex | Hippocampus |
| Vehicle | 100.0 ± 11.9 | 100.0 ± 12.9 | 100.0 ± 15.4 | 100.0 ± 8.0 |
| Ebselen (0.5 mg kg$^{-1}$) | 83.3 ± 14.4 | 129.8 ± 12.9 | 105.0 ± 10.3 | 210.2 ± 35.1** |
| Ebselen (1 mg kg$^{-1}$) | 75.9 ± 6.3 | 141.0 ± 9.5 | 122.7 ± 20.6 | 128.5 ± 13.6 |
| Ebselen (5 mg kg$^{-1}$) | 88.7 ± 3.8 | 139.2 ± 17.0 | 131.9 ± 14.5 | 135.4 ± 17.2 |

Data shown are mean ± SEM values.
*p < 0.05, p < 0.005, *p < 0.001 Vehicle vs Ebselen.
One-way ANOVA followed by post-hoc Dunnett's test, n = 5-6.

Summary

The Inventors have compared the effects of ebselen and lithium in a mouse behavioural model (HTR and ESR) and molecular model (cortical IEG expression) of 5-HT$_{2A}$ receptor function. The data demonstrate that both ebselen and lithium reduced 5-HT$_{2A}$ receptor function in both models. The IMPase inhibitor L-690,330 also reduced 5-HT$_{2A}$ receptor function whereas the GSK-3 inhibitor AR-A014418 did not, and IMPase inhibition is proposed as a likely mechanism for the activity of both ebselen and lithium. Finally, in microdialysis experiments ebselen potentiated the increase in extracellular 5-HT induced by the SSRI citalopram, an effect previously shown for lithium and 5-HT$_{2A}$ antagonists (Wegener et al., 2003, Psychopharmacology 166: 188-194; Boothman et al., 2006, Neuropharmacology 50: 726-732). The effect of ebselen was associated with other neurochemical evidence that the drug increased 5-HT formation, as also demonstrated for lithium in earlier work (eg. Knapp & Mandell, 1973, Science 180: 645-647). Overall these data suggest that ebselen has lithium-like effects on 5-HT$_{2A}$ receptor function, and provides evidence for the therapeutic application of ebselen in SSRI augmentation.

The invention claimed is:

1. A method of treating or controlling treatment-resistant depressive disorder, the method comprising administering to a subject in need thereof a pharmaceutical composition comprising a therapeutically effective amount of a compound of Formula I, or a pharmaceutically acceptable salt thereof,

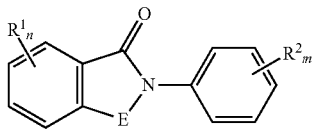

Formula I wherein:
E is S or Se;
R¹ and R² are optional substituents, and are at each occurrence independently selected from:
(4) a halogen, which is preferably selected from F, Cl and Br;
(5) $C_1$-$C_4$ alkyl, such as $C_1$-$C_2$ alkyl or $C_1$ alkyl, optionally substituted with one or more halogen atoms, each of which is preferably selected from F, Cl and Br; and
(6) $C_1$-$C_4$ alkoxy, such as $C_1$-$C_2$ alkoxy or $C_1$ alkoxy; optionally substituted with one or more halogen atoms, each of which is preferably selected from F, Cl and Br;
m is an integer in the range of from O to 5; and
n is an integer in the range of from O to 4.

2. A method of treating or controlling treatment-resistant depressive disorder, the method comprising administering to a subject in need thereof a therapeutically effective amount of: a) a compound of Formula I, or a pharmaceutically acceptable salt thereof,

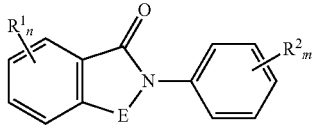

Formula I wherein:
E is S or Se;
R¹ and R² are optional substituents, and are at each occurrence independently selected from:
a halogen, which is preferably selected from F, Cl and Br;
$C_1$-$C_4$ alkyl, such as $C_1$-$C_2$ alkyl or $C_1$ alkyl, optionally substituted with one or more halogen atoms, each of which is preferably selected from F, Cl and Br; and
$C_1$-$C_4$ alkoxy, such as $C_1$-$C_2$ alkoxy or $C_1$ alkoxy; optionally substituted with one or more halogen atoms, each of which is preferably selected from F, Cl and Br;
m is an integer in the range of from O to 5; and
n is an integer in the range of from O to 4; and b) one or more additional antidepressants or a pharmaceutically acceptable salt thereof.

3. The method according to claim 1, wherein the compound of Formula I or salt thereof is 2-phenyl-1,2-benzisoselenazol-3(2H)-one (ebselen) or 2-phenyl-1,2-benzisothiazol-3(2H)-one, or a pharmaceutically acceptable salt thereof.

4. The method according to claim 1, wherein the compound of Formula I or salt thereof is 2-phenyl-1,2-benzisoselenazol-3(2H)-one (ebselen) or a pharmaceutically acceptable salt thereof.

5. The method according to claim 2, wherein the compound or pharmaceutically acceptable salt of Formula I and the one or more additional antidepressants, or a pharmaceutically acceptable salt thereof, are for separate or simultaneous administration.

6. The method according to claim 2, wherein the one or more additional antidepressants are selected from: Selective Serotonin Reuptake Inhibitors (SSRIs), including citalopram, dapoxetine, escitalopram, fluoxetine, fluvoxamine, paroxetine and sertraline; and the related compound, vortioxetine;
Tricyclic antidepressants (TCAs), including amitriptyline, clomipramine, dosulepin, doxepin, imipramine, lofepramine, and nortriptyline; and the related compound trazodone;
Serotonin and Noradrenaline Reuptake inhibitors (SNRis), including duloxetine, and venlafaxine;
Noradrenergic and Specific Serotonergic Antidepressants, including mirtazapine;
Monoamine oxidase inhibitors (MAOIs), including moclobemide, phenelzine, tranylcypromine, isocarboxazid;
Selective Noradrenaline Reuptake Inhibitors (NARI), including reboxetine;
Noradrenaline and Dopamine Reuptake Inhibitors (NDRI), including bupropion;
Melatonin agonists and 5-HT2C receptor antagonists, including agomelatine; and
Lithium; or a pharmaceutically acceptable salt thereof.

7. The method according to claim 6, wherein the one or more additional antidepressants are selected from: citalopram, dapoxetine, escitalopram, fluoxetine, fluvoxamine, paroxetine, sertraline, vortioxetine, amitriptyline, clomipramine, dosulepin, doxepin, imipramine, lofepramine, nortriptyline, trazodone, duloxetine, venlafaxine, mirtazapine, moclobemide, phenelzine, tranylcypromine, isocarboxazid reboxetine, bupropion, agomelatine, and lithium; or a pharmaceutically acceptable salt thereof.

8. The method according to claim 2, wherein the compound of Formula I or salt thereof is 2-phenyl-1,2-benzisoselenazol-3(2H)-one (ebselen) or 2-phenyl-1,2-benzisothiazol-3(2H)-one, or a pharmaceutically acceptable salt thereof.

9. The method according to claim 2, wherein the compound of Formula I or salt thereof is 2-phenyl-1,2-benzisoselenazol-3(2H)-one (ebselen) or a pharmaceutically acceptable salt thereof.

* * * * *